US006861214B1

(12) United States Patent
Rampal et al.

(10) Patent No.: US 6,861,214 B1
(45) Date of Patent: Mar. 1, 2005

(54) IMMOBILIZATION OF BIOPOLYMERS TO AMINATED SUBSTRATES BY DIRECT ADSORPTION

(75) Inventors: Jang B. Rampal, Yorba Linda, CA (US); Robert S. Matson, Orange, CA (US)

(73) Assignee: Beckman Coulter, Inc., Fullerton, CA (US)

(*) Notice: Subject to any disclaimer, the term of this patent is extended or adjusted under 35 U.S.C. 154(b) by 0 days.

(21) Appl. No.: 09/694,701

(22) Filed: Oct. 23, 2000

(51) Int. Cl.[7] .............................. C12Q 1/68; A61L 9/00; B32B 27/04; A62B 7/08; B01J 19/08

(52) U.S. Cl. .................................. 435/6; 422/5; 422/50; 422/61; 422/71; 422/88; 422/99; 422/122; 422/131; 422/186

(58) Field of Search .............................. 422/88, 89, 50, 422/61, 101, 122, 131, 5, 71, 73, 99, 186, 186.05; 435/6

(56) References Cited

U.S. PATENT DOCUMENTS

| | | | | |
|---|---|---|---|---|
| 4,588,682 | A | * 5/1986 | Groet et al. ................... | 435/6 |
| 4,818,681 | A | 4/1989 | Dattagupta .................... | 435/6 |
| 4,877,745 | A | 10/1989 | Hayes et al. ................ | 436/166 |
| 5,024,933 | A | 6/1991 | Yang et al. .................... | 435/6 |
| 5,112,736 | A | 5/1992 | Caldwell et al. ............... | 435/6 |
| 5,215,882 | A | 6/1993 | Bahl et al. ..................... | 435/6 |
| 5,445,934 | A | 8/1995 | Fodor et al. .................... | 435/6 |
| 5,554,501 | A | 9/1996 | Coassin et al. ................ | 435/6 |
| 5,585,275 | A | 12/1996 | Hudson et al. ............. | 436/518 |
| 5,610,287 | A | 3/1997 | Nikiforov et al. ......... | 536/24.3 |
| 5,622,826 | A | * 4/1997 | Varma .......................... | 435/6 |
| 5,723,320 | A | 3/1998 | Dehlinger .................. | 435/91.1 |
| 5,843,789 | A | 12/1998 | Nomura et al. ............ | 436/164 |
| 5,965,352 | A | 10/1999 | Stoughton et al. ............. | 435/4 |
| 5,981,185 | A | 11/1999 | Matson et al. ................. | 435/6 |

(List continued on next page.)

OTHER PUBLICATIONS

David F. Waugh, et al., "Interactions of Bovine Thrombin and Plasma Albumin with Low–Energy Surfaces," Journal of biomdicall Materials Research, vol. 12, pp. 599–625, 1978.

Bradley Stevenson, et al., "Cloning of 5' cDNA Regions by Inverse PCR," Circle Reader Service No. 146, 1994.

R. Sipehia, et al., "Immobilization of Enzymes on Polypropylene Bead Surfaces by Anhydrous Ammonia Gaseous Plasma Technique," Journal of Biomedical Materials Research, vol. 22, pp. 417–422, 1988.

(List continued on next page.)

*Primary Examiner*—Kenneth R. Horlick
*Assistant Examiner*—Joyce Tung
(74) *Attorney, Agent, or Firm*—William H. May; D. David Hill; Hogan & Hartson

(57) ABSTRACT

An assay article for detection biopolymers contained in a sample is described. The assay article includes a substrate and a biopolymer directly adsorbed on the surface of the substrate. A plurality of biopolymers may be adsorbed on the surface of the substrate to form an array. Also disclosed is a method of making the assay article. In the preferred method, an aminated polypropylene substrate is used. A biopolymer is contacted with the aminated substrate under a condition sufficient for direct adsorption of the biopolymer on the surface of the substrate. A method of detecting a target biopolymer contained in a sample is also disclosed. In this method, a substrate is contacted with either a probe or target biopolymer under a condition sufficient for a direct adsorption of either the probe or target biopolymer on the substrate to form a probe assay article or a target assay article. Then, the probe assay article is contacted with the target biopolymer, or the target assay article is contacted with the probe biopolymer under a condition that allows the formation of a probe-target complex. Finally, the complex is detected and the presence of the complex is used as a measurement for the presence or the amount of the biopolymer target contained in the sample.

29 Claims, 2 Drawing Sheets

U.S. PATENT DOCUMENTS

| | | | | |
|---|---|---|---|---|
| 6,013,789 A | | 1/2000 | Rampal | 536/25.3 |
| 6,048,695 A | | 4/2000 | Bradley et al. | 435/6 |
| 6,197,501 B1 | * | 3/2001 | Cremer et al. | 435/6 |
| 6,322,968 B1 | * | 11/2001 | Head et al. | 435/6 |

OTHER PUBLICATIONS

Bio Techniques, "Reduction of Enzyme Adsorption to Polypropylene Surfaces in the Presence of Nonionic Detergent," vol. 17, No. 6, pp. 1048–1049, 1994.

Ronald C. Chatelier, et al., "Covalent Attachment and Non–Specific Binding of Reactive Probe Molecules onto Surfaces," J. Biomater Sci. Polymer Edn., vol. 7, pp. 601–622, 1995.

L. Stanislawski, et al., "Plasma Protein Adsorption to Artificial Ligament Fibers," Journal of Biomedical Materials Research, vol. 29, pp. 315–323, 1995.

R. Ganapathy, et al., "Immobilization of $\alpha$–Chymotrypsin on Oxygen–RF–Plasma Functionalized PET and PP Surfaces," J. Biomater. Sci. Polymer Edn., vol. 9, No. 4, pp. 389–404, 1998.

* cited by examiner

IMMOBILIZATION OF BIOPOLYMERS TO AMINATED SUBSTRATES BY DIRECT ADSORPTION

AREA OF THE ART

The present invention relates generally to solid substrates with immobilized biopolymers. In particular, the invention relates to aminated substrates with adsorbed biopolymers, methods of their construction and methods of their use in detection of target biopolymers.

DESCRIPTION OF THE PRIOR ART

Analysis of unknown biopolymers targets often involves their specific binding to known biopolymers probes. The most common technique employing immobilized biopolymers is the Southern blot hybridization technique, in which a set of DNA targets is immobilized on a membrane and a solution containing labeled DNA probe molecules is used to bathe the membrane under conditions where complementary molecules will anneal. In an analogous technique called Northern blot hybridization, RNA targets are immobilized on membranes and anneal to complementary RNA probes. Reverse blot hybridization employs the opposite approach. Instead of immobilizing DNA targets, a set of DNA probes is immobilized on a solid surface and the unknown labeled DNA target is present in the liquid phase.

Arrays, constructed by attaching a plurality of the same or different biopolymers to discrete isolated areas on the surface of the substrate, are becoming increasingly important tools in analysis of unknown biopolymers, such as gene expression analysis, DNA sequencing, mutation detection, polymorphism screening, linkage analysis, genotyping single nucleotide polymorphisms (SNPs), and screening for alternative splice variants in gene transcripts.

Gene expression analysis is a method of critical importance to basic molecular biological research. Since in higher organisms, the choice of genes being expressed in any given cell has a profound effect on the nature of the cell, gene expression analysis can.: provide a key to diagnosis, prognosis, and treatment of a variety of diseases in animals, including humans and plants. Additionally, gene expression analysis can be used to identify differentially-expressed novel genes, to correlate a gene expression to a particular phenotype, to screen for a disease predisposition, and to conduct toxicity testing.

Typically, in the gene expression analysis. an array of probe nucleic acids is formed by attaching a set of individual gene-specific probes to a solid substrate in a regular pattern, so that the location of each probe is known. The array is contacted with a sample containing target nucleic acids under hybridization conditions. The hybrids are detected using a wide variety of methods, most commonly by employing radioactive or fluorescent labels.

There are two general methods of forming polynucleotide arrays for the gene expression analysis. The first method involves in situ synthesis of oligonucleotides in predetermined positions of a solid substrate. The second method includes the association of pre-synthesized oligonucleotides or polynucleotides with a solid substrate. In situ syntheses of oligonucleotides on glass modified with an aliphatic polyether linker (Southern, E. M. et al., Genomics 13:1008, 1992) and polypropylene as a solid substrate (U.S. Pat. No. 5,554,501) have been reported. The in situ method, however, suffers from certain shortcomings. For example, since the addition of each nucleotide is a separate reaction, the reproducibility and reaction yield may vary widely between different locations on the substrate, as well as between different substrates. Consequently, it is hard to obtain accurate and reproducible data with arrays formed by direct synthesis.

Alternatively, pre-synthesized polynucleotides may be immobilized on a substrate by ultraviolet cross-linking, chemical adhesion, or covalent bonding. Typically, a polynucleotide, a solid substrate, or both, are derivatized to initiate such immobilization. Usually it is preferred that the solid substrate is capable of immobilizing probe DNA, while being substantially inert to any other DNA. Glass is a commonly used solid substrate, because it is inexpensive and of good optical quality. Various types of pre-derivatized glass substrates are commercially available, including microscope slides coated with poly-L-lysine or amino propyl silane, or glass slides with exposed aldehyde functionalities. However, the derivatization of a glass surface creates a positive electrostatic net charge, which results in undesirable non-specific electrostatic binding of nucleic acids to the solid substrate during subsequent hybridization procedures. Numerous other surface coatings for efficient immobilization of polynucleotides have been proposed and include an isolate of the naturally occurring mussel adhesive protein (U.S. Pat. No. 5,024,933), nucleoside phosphate (U.S. Pat. No. 4,818,681), and salt or cationic detergent (U.S. Pat. No. 5,610,287), to name a few. These methods, however, also entail unspecific binding of nucleic acids on the substrates. Such unspecific binding of DNA makes interpretation of the hybridization results difficult.

Polynucleotides themselves can be derivatized prior to the binding to a solid substrate. For example, U.S. Pat. No. 6,048,695 describes epoxide-modified DNA which is readily affixed to an unmodified solid substrate. such as an underivatized glass surface. Finally, both a polynucleotide and a solid substrate may be modified to allow efficient covalent bonding. For example, U.S. Pat. No. 5,215,882 discloses modifying a nucleic acid with a primary amine or equivalent, followed by the reaction of the modified nucleic acid with the solid substrate having free aldehyde groups in the presence of a reducing agent. However, the derivatization of polynucleotides and their subsequent covalent binding to solid substrates are long and tedious processes. Consequently, the arrays produced by conventional techniques are fairly expensive ($6–$36 per slide). Similar problems exist in respect to immobilization of other biopolyrners on solid substrates.

In summary, the conventional immobilization methods do not provide desirable fast hybridization and high specificity of binding of targets to probes. Additionally, currently available methods of manufacturing assay articles for use in biopolymer detection are slow, tedious, and economically unfavorable.

SUMMARY OF THE INVENTION

Accordingly, it is an object of the invention to provide a cost-efficient, rapid and convenient method of making an assay article and a method of using such an assay article for a biopolymer detection. Particularly, it is an object of the present invention to develop a method of making an assay article by direct adsorption of biopolymers on solid substrates.

The present invention is based on the discovery that modified substrates, and particularly plasma aminated polypropylene substrates are capable of direct and stable adsorption of nucleic acids, proteins, polypeptides, and their analogues without chemical crosslinking. Consequently, one aspect of the present invention provides a method of making an assay article for use in biopolymer detection. The method comprises the steps of:

(a) providing a biopolymer;
(b) providing an aminated substrate; and
(c) contacting the biopolymer with a surface of the aminated substrate under a condition sufficient for a direct adsorption of the biopolymer on the surface of the substrate.

According to embodiments of the present invention, the substrate may be fabricated in a form of foams, filaments, threads, sheets, films, slides, gels, membranes, beads, plates, and like structures. In one embodiment of the present invention, the step of providing the biopolymer includes providing a solution of the biopolymer; and the step of contacting the biopolymer comprises:

(a) placing an aliquot of the biopolymer solution on the substrate; and
(b) air-drying the substrate to directly adsorb the biopolymer on the surface of the substrate.

In accordance with one embodiment of the present invention, a plurality of biopolymers may be placed and adsorbed on the surface of the aminated polypropylene substrate in an array.

Another aspect of the present invention provides a method of detecting a target biopolymer contained in a sample. The method comprises the steps of:

(a) providing an aminated substrate;
(b) providing a probe biopolymer that can form a complex with the target biopolymer;
(c) contacting either the probe or target biopolymer with a surface of the aminated substrate under a condition sufficient for a direct adsorption of either the probe or target biopolymer on the substrate surface to form a probe assay article or a target assay article, respectively;
(d) contacting the probe assay article with the target biopolymer, or contacting the target assay article with the probe biopolymer under a condition that allows the formation of a complex comprising the probe and the target biopolymers; and
(e) detecting and determining the presence of the complex as a measurement for the presence or the amount of the target biopolymer contained in the sample.

The complex of the probe and the target biopolymers may also include a reporter. The reporter may be selected from a group consisting of: dyes, chemiluminescent compounds, enzymes, fluorescent compounds, metal complexes, magnetic particles, biotin, hapten, radio frequency transmitters, and radioluminescent compounds. An assay article may be formed by attaching the same or different unmodified probes or target biopolymers to discrete areas of the substrate to produce an array. The signal produced by the report molecules immobilized on the array may be detected and recorded by a number of means, such as a laser with a confocal array reader, phosphor imager, or a CCD camera.

A further aspect of the present invention provides an assay article for detecting biopolymers. The assay article comprises a substrate and a biopolymer directly adsorbed on the surface of the substrate. In one embodiment, a plurality of the same or different biopolymers is attached to discrete, isolated areas of the substrate by direct adsorption to form an array.

Another aspect of the present invention provides a test kit for detecting a target biopolymer contained in a sample. The kit comprises an aminated polypropylene substrate and a probe biopolymer directly adsorbed on a surface of the substrate. When the probe polymer is contacted with the target biopolymer, they form a complex that can be detected by utilizing reporters and signal detection devices.

The present invention is well-suited for use in creating biopolymer arrays and polynucleotide arrays, such as gene expression micro-arrays for use in gene expression analysis, in particular. The polynucleotide arrays may be used for the evaluation or identification of biological activity. The present invention may also be used in creating polynucleotide arrays for the purpose of polynucleotide sequencing. Further, the assay articles of the present invention may contain a range of adsorbed biopolymers and may be utilized in hybridization assays and immunoassays.

The present invention provides many advantages. Since the invention allows for the adsorption of biopolymers directly on a solid substrate without chemical crosslinking, costly production of modified biopolymers, such as thiol- or amino-modified DNA, may be avoided. Also, the task of making arrays is greatly simplified and the production costs are significantly reduced, because the biopolymers are simply air-dried on the substrate.

DESCRIPTION OF THE FIGURES

The above-mentioned and other features of this invention and the manner of obtaining them will become more apparent, and will be best understood by reference to the following description, taken in conjunction with the accompanying FIG. 1.

DETAILED DESCRIPTION OF THE INVENTION

Figure 1:
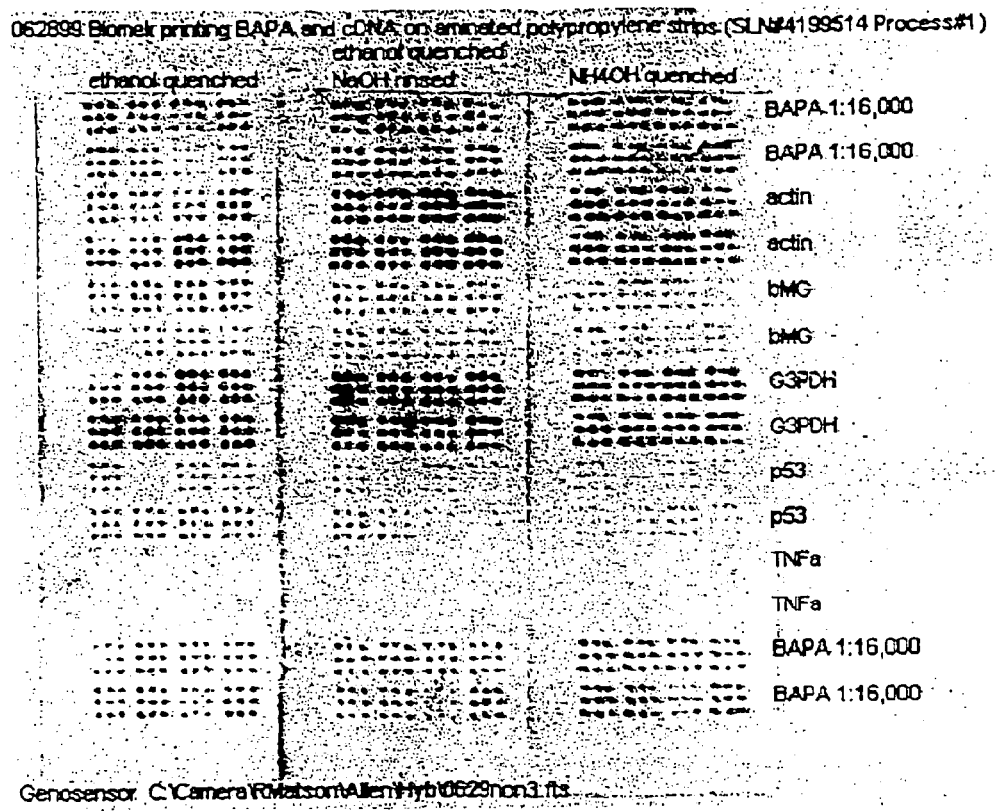
FIG. 1 shows the hybridization results of labeled target cDNA from actin, β-microglobulin, G3PDH, and p53 with their corresponding probe cDNA immobilized on polypropylene substrates. TNF-α immobilized on the substrate was used as a control for a non-specific hybridization.

One aspect of the present invention provides a method of making an assay article for use in biopolymer detection. The method comprises the steps of:

(a) providing a biopolymer;
(b) providing an aminated substrate; and
(c) contacting the biopolymer with a surface of the aminated substrate under a condition sufficient for a direct adsorption of the biopolymer on the surface of the substrate.

The term "biopolymer" as used herein refers to nucleic acids, polynucleotides, polypeptides, proteins, and analogues thereof. As used herein, "polynucleotide" refers to a polymer of deoxyribonucleotides or ribonucleotides, in the form of a separate fragment or as a component of a larger construction. "Polynucleotide", as used herein, may be DNA, RNA, or a DNA analog, such as PNA (peptide nucleic acid). The DNA may be a single- or double-stranded DNA, or a DNA amplified by PCR technique. The RNA may be a mRNA. The length of the polynucleotides may be from about 20 bp to about 10 kb. In accordance with one embodiment of the present invention, the polynucleotide is a complementary DNA (cDNA). The length of a cDNA polynucleotide may be in the range of about 100 bp to about 10 kb, preferably, 200 bp to 1000 bp.

As used herein, "polypeptide" refers to a polymer of amino acids, wherein the α-carboxyl group of one amino acid is joined to the α-amino group of another amino acid by a peptide bond. A protein may comprise one or multiple polypeptides, linked together by disulfied bonds. Examples of the protein include, but are not limited to, antibodies, antigens, ligands, receptors, etc.

It is a discovery of the present invention that biopolymers may be attached to substrates by direct adsorption and without any chemical cross-linking with the substrate. We found that polypropylene substrates are particularly useful for direct adsorption. The direct adsorption is further improved by modifying the substrates prior to contacting them with biopolymers. The substrates may be modified by introducing a functionality selected from a group consisting of: amino, carboxyl, thiol, and their derivatives. In one embodiment, the substrate is modified by introduction of an amine group.

The methods for introduction of amine groups onto the polypropylene surface are described in the commonly assigned U.S. Pat. No. 6,013,789, the relevant content of which is incorporated herein in its entirety by reference. In short, amino groups may be introduced onto the surface of a polypropylene medium by using a plasma discharge in an ammonia- or organic-amine- containing gas. The "plasma" is most preferably an ionized gas, which gains sufficient ionization energy from an electromagnetic field. Preferably, the ionization energy is applied by a radio-frequency plasma discharge, a microwave frequency plasma discharge, or a corona discharge. In a particularly preferred embodiment of the invention, the amine is derived from an ammonia gas and the elevated energy state is achieved via radio-frequency plasma discharge. The aminated polypropylene is then utilized for direct adsorption of a pre-synthesized biopolymer.

In order to accommodate a number of different testing techniques including specialized testing equipment, aminated polypropylene substrates may be molded into any of a variety of shapes and forms. Examples of such shapes and forms of the aminated polypropylene substrates include, but are not limited to, foams, filaments, threads, sheets, films, slides, gels, membranes, beads, plates, and like structures. An aminated polypropylene substrate may be fabricated in the form of a planar device having discrete isolated areas in the form of wells, troughs, pedestals, hydrophobic or hydrophilic patches, die-cut adhesive reservoirs or other physical barriers to fluid flow. Examples of such a substrate include, but are not limited to, a microplate or the like. Because the substrate of the present invention is particularly useful in the preparation of biopolymer arrays for the evaluation or identification of biological activity, the aminated polypropylene substrate is preferably in the form of a device having at least one flat planar surface. Examples of such devices with flat surfaces include, but are not limited to, slides, sheets, films, or the like.

The size of the substrate can vary and depends upon the final use of the immobilized biopolymers. Those skilled in the art will appreciate that arrays of biopolymers immobilized on miniaturized solid supports have been under development for many years. These solid supports can be measured in terms of $mm^2$ planar surface area and can have numerous different immobilized biopolymers, each attached to a different site-specific location on the miniaturized solid support. Solid supports in the form of dipsticks and slides are also within the scope of the present invention. As known in the art, dipsticks typically are rectangular in shape with each side measuring a few centimeters.

Since the instant methods of assay article formation involve direct adsorption of biopolymers on substrates, no chemical modification to biopolymers is required. Here, the term "direct adsorption" means adsorption without any chemical linkers. Unlike the related art, which uses chemical crosslinking of biopolymers to the substrates, the present invention allows immobilization of both unmodified and modified biopolymers on substrates by simple air-drying on the substrate. For the purpose of the present invention, "unmodified biopolymer" means native biopolymer, and "modified biopolymer" means a biopolymer with introduced functional groups. For example, a modified biopolymers may be biotinylated or aminated DNA.

In present invention, a biopolymer is immobilized on a substrate by contacting the biopolymer with the substrate under a condition sufficient for a direct adsorption of the biopolymer to the substrate. A condition is sufficient if it allows the biopolymer to become adsorbed on the surface of the substrate in a stable way. While not wanting to be bound by the theory, it is believed that, under the conditions of the present invention, biopolymers may be adsorbed on a substrate by ionic and hydrophobic interaction.

For the purpose of the present invention, it is not crucial which particular method is used to carry out the step of contacting the biopolymer with the substrate. In accordance with embodiments of the present invention, the contacting step may be carried out by jet printing, solid or open capillary device contact printing, microfluidic channel printing, silk screening, and printing using devices based upon electrochemical or electromagnetic forces. For example, thermal inkjet printing techniques utilizing commercially available jet printers and piezoelectric microjet printing techniques, as described in U.S. Pat. No. 4,877,745, may be utilized to spot polynucleotides to the aminated substrates. A Biomek High Density Replicating Tool (HDRT) (Beckman Coulter, CA) may also be used for an automatic gridding. Alternatively, the contacting step may be carried out by manual spotting of the biopolymers on the aminated substrate. Examples of manual spotting include, but are not limited to, manual spotting with a pipettor. It should be understood that the aminated substrate of the present invention may be exposed to biopolymers by any methods as long as the biopolymers are put in direct contact with the substrate.

In accordance with embodiments of the present invention, the step of providing the biopolymer may include providing a solution of the biopolymer. The step of contacting the biopolymer with aminated substrate may include:

(a) placing an aliquot of the biopolymer solution on the substrate; and (b) air-drying the substrate to directly adsorb the biopolymer on the surface of the substrate.

The solution of the biopolymer may be any solution that delivers the biopolymers to the surface of the substrate. Preferably, the solvent is an aqueous buffer having a pH from about 4 to about 13. In one embodiment, the biopolymer is a polynucleotide, and a solution of the polynucleotides in 50 mM sodium bicarbonate, pH 9, is spotted on the aminated substrate.

The concentration of biopolymers contained in aqueous solutions may vary, depending on the type of molecule, the molecule size, the molecule structure, and other factors that may influence solubility of the molecules. Preferably, the amount of the biopolymers applied to the substrate ranges from about $10^{-20}$ to about $10^{-14}$ moles. For example, in one embodiment, the biopolymer is a polynucleotide, and the amount of the polynucleotide applied to the substrate is about $10^{-18}$, moles. The size of the biopolymer solution aliquot is not crucial, as long as it provides sufficient amount of the biopolymer. Consequently, the size of the aliquots applied to the aminated substrate may vary, depending on the concentration of the biopolymer in the solution and the assay needs. For example, the aliquot may be from about 0.1 nL to about 500 nL. In one embodiment, the biopolymer is a polynucleotide, and aliquots of about 10 nL of the 1 nM polynucleotide solutions are placed on the aminated substrate.

In accordance with the present invention. the air-drying step is conducted for a period of time sufficient to allow adsorption of the biopolymer solution. The length of the air-drying time depends on the volume of the aliquots applied to the substrate, room temperature and humidity. For micro- and nanoliter aliquots, the air-drying step may take from about 5 to about 60 minutes. For example in one embodiment, 10 nL aliquots are placed on the surface of the aminated substrate and dried at 22° C. for one hour or for about fifteen minutes at 35° C.

As mentioned above, many applications for utilizing immobilized biopolymers require biopolymers to be immobilized at site-specific locations on a substrate surface. Accordingly, in the present invention, a plurality of biopolymers may be placed and adsorbed on the surface of the aminated polypropylene substrate in an array. In order to prepare ordered arrays of biopolymers with each biopolymer located at site-specific locations, including grids and 1×n arrays of immobilized biopolymers, a preselected site on the surface of the substrate is exposed to a solution of the desired biopolymer. In accordance with the present invention, this can be accomplished manually by applying an aliquot of biopolymer solution to a preselected location on the substrate. Alternatively, thermal inkjet printing techniques utilizing commercially available jet printers and piezoelectric microjet printing techniques, as described in U.S. Pat. No. 4,877,745, can be utilized to spot selected substrate surface sites with selected biopolymers.

A wide variety of array formats may be employed in accordance with the present invention. One particularly useful format is a linear array of nucleic acid probes, generally referred to in the art as a dipstick. Another suitable format comprises a two-dimensional pattern of discrete cells. Of course, as would be readily appreciated by those skilled in the art, other array formats would be equally suitable for use in accordance with the present invention.

The array of the present invention may be a part of a variety of devices, such microtiter plates, test tubes, inorganic sheets, dipsticks, etc. For example, when the substrate is a thread, one or more of such threads can be affixed to a plastic dipstick-type device. When the substrate is in a form of a membrane, it can be affixed to glass slides. The particular device is, in and of itself, unimportant, as long as the substrate is securely affixed to the device without affecting the functional behavior of the substrate or any adsorbed biopolymer. The device should also be stable to any materials into which the device is introduced (e.g., clinical samples. etc.).

The method of making an assay article may further include a step of exposing the assay article to a reagent, such as ammonium hydroxide, ethanol, or protein. In a preferred embodiment of this invention ethanol is used for nucleic acid arrays and casein is used for protein arrays.

Direct adsorption of biopolymers on aminated polypropylene substrates is wellsuited for use in the construction of genosensors and other array-based systems, such as differential gene expression micro-arrays. An aminated polypropylene substrate with the adsorbed biopolymers of the present invention may also be used as a device for performing a ligand binding assay or for performing a hybridization assay by either reverse hybridization (probes attached) or southern blot (target attached). Such a device may also be used in an immunoassay.

Accordingly, another aspect of the present invention provides a method of detecting a target biopolymer contained in a sample. The method comprises the steps of:

(a) providing an aminated substrate;

(b) providing a probe biopolymer that can form a complex with the target biopolymer;

(c) contacting either the probe or target biopolymer with a surface of the aminated substrate under a condition sufficient for a direct adsorption of either the probe or target biopolymer on the substrate surface to form a probe assay article or a target assay article, respectively;

(d) contacting the probe assay article with the target biopolymer, or contacting the target assay article with the probe biopolymer under a condition that allows the formation of a complex comprising the probe and the target biopolymers; and (e) detecting and determining the presence of the complex as a measurement for the presence or the amount of the target biopolymer contained in the sample.

For the purpose of the present invention, probe biopolymer recognizes and binds to the target biopolymer forming a probe-target complex. Both the probe and the target biopolymers may be selected from a group consisting of nucleic acids, polypeptides, proteins, and their analogues. For example, when the target is a polynucleotide, the probe may comprise a polynucleotide that is complimentary to the target polynucleotide (see FIG. 1). When the target is a receptor or a ligand, the probe may comprise a ligand or a receptor that respectively recognizes and binds to the target receptor ligand. When the target is an antigen, the probe may comprise an antibody that recognizes the antigen, or vice versa (see FIG. 2).

Either target or probe may be directly adsorbed on the substrate. For example, in the Southern blot or Northern blot applications, targets are adsorbed on the substrate. Then, the substrate with the adsorbed targets is contacted with the probes, preferably labeled, to detect the target biopolymers. To the contrary, in Ligand Binding assays or Affinity Purification assays, probes are bound to the substrate first. Then, target contained in a sample solution is contacted with the probes adsorbed on the substrate.

For the purpose of the present invention, an adsorption condition is sufficient if the probe or target can adsorb on the substrate. Such a condition may vary, depending on the type of the biopolymers and their size. For instance, in one embodiment, described in detail in the following Example 1, 10 nl aliquots of cDNA solutions are applied to an aminated polypropylene substrate. Following the application of the cDNA, the substrates are dried at 35° C. for 15 minutes. Then, the substrates are either soaked in ethanol for one hour or in ammonium hydroxide for 15 minutes to remove loosely bound nucleic acid. Finally, the slides are briefly rinsed with water and air-dried. One skilled in the art can readily determine the suitable conditions for adsorbing other probes or targets in view of the teaching of the present invention. As discussed above, a variety of substrates may be used. In a preferred embodiment, however, aminated polypropylene substrates are used.

Contacting the probes with the targets (or hybridization) is conducted under conditions that allow the formation of stable complexes between probes and targets. For example, when target polynucleotides are contacted with probe polynucleotides adsorbed on an aminated polypropylene substrate, complementary regions on the target and the probe polynucleotides anneal to each other, forming probe-target complex. The selection of such conditions is within the level of skill in the art and include those in which a low, substantially zero, percentage of mismatched hybrids. form. The precise conditions depend, however, on the desired selectivity and sensitivity of the assay. Such conditions include, but are not limited to, the hybridization temperature, the ionic strength and viscosity of the buffer, and the respective concentrations of the target and probe biomolecules. Hybridization conditions may be initially chosen to correspond to those known to be suitable in standard procedures for hybridization to filters and then optimized for use with the aminated polypropylene substrates of the present invention. The conditions suitable for hybridization of one type of target material would appropriately be adjusted for use with other target materials.

For example, in certain embodiments the target polynucleotides are hybridized to the probe polynucleotides at temperatures in the range of about 20° C. to about 70° C., for a period from about 1 hour to about 24 hours, in a suitable hybridization buffer. Suitable hybridization buffers for use in the practice of the present invention generally contain a high concentration of salt. A typical hybridization buffer contains in the range of about 2× to about 6×SSC and about 0.01% to about 0.5% SDS at pH 7–8. Once the probe/target complex is formed, the substrates are washed under conditions suitable to remove substantially all non-specifically bound target or probe biopolymers. Preferably, the washing is carried out at a temperature in the range of about 20° C.–70° C. with a buffer containing about 0.1–6×SSC and 0.01–0.1% SDS. The most preferred wash conditions for polynucleotides presently include a temperature, which is the same as hybridization temperature, and a buffer containing 2×SSC and 0.01% SDS. As previously noted, it would be a routine matter for those working in the field to optimize the contacting (hybridization) conditions for any given combination of target and probe biopolymers.

In accordance with embodiments of the present invention, either the targets or probes of the present invention may be labeled with a reporter. Delectability may be provided by such characteristics as color change, luminescence, fluorescence, or radioactivity. Examples of reporters include, but are not limited to, dyes, chemiluminescent compounds, enzymes, fluorescent compounds, metal complexes, magnetic particles, biotin, haptens, radio frequency transmitters, and radioluminescent compounds. One skilled in the art can readily determine the type of reporter to be used once the type of target or probe biopolymers is determined.

The labeling procedure may occur prior to analysis (direct labeling) or after hybridization (indirect labeling). An example of indirect labeling would be the biotinylation of a target polynucleotide, hybridizing it with a probe, and reacting the target-probe complexes with a streptavidin-alkaline phosphatase conjugate. The biotin moieties retained after the hybridization with probe polynucleotides bind to a streptavidin-alkaline phosphatase conjugate, which then acts on a chromogenic substrate, such as Enzyme Labeled Fluorescent (ELF) reagent.

For the purpose of the present invention, the same or different biopolymers may be attached to the substrates. If the biopolymers are different, preferably they are located in isolated areas of the substrate to form arrays. For example, a substrate may be a microplate. Different biopolymers may be adsorbed within different wells of the microplate for forming arrays. In accordance with another embodiment of the present invention, the substrate may be a slide and different biopolymers are adsorbed on different areas of the slide to form an array.

The signal produced by an array may be detected by a naked eye or by means of a specially designed instrumentation, such as a confocal array reader. For example, in one embodiment, a fluorescent signal is recorded with a charged coupled device (CCD) camera. It would be appreciated by those skilled in the art, that the choice of a particular method used to detect and quantify the signal is not crucial for this invention. Essentially, any detection method may be used as long as it provides consistent and accurate results.

Another aspect of the present invention provides an assay article for detecting target biopolymers. The assay article of the present invention comprises a substrate and a biopolymer directly adsorbed on the surface of the substrate.

The substrate may be made of a variety of materials. In one embodiment the substrate is made of polypropylene or polyethylene. Polypropylene and polyethylene are organic materials that can be surface activated, but otherwise are chemically inert under harsh chemical conditions. Polypropylene can be used in very corrosive environments. For example, polypropylene has good chemical resistance to a variety of mineral acids (e.g., hydrochloric acid), organic acids (e.g., formic acid, acetic acid), bases (e.g., ammonium hydroxide, potassium hydroxide), salts (e.g., sodium chloride), oxidizing agents (e.g., peracetic acid, iodine solutions), and organic solvents (e.g. acetone, ethyl alcohol, acetonitrile, dichloromethane, etc.). Additionally, polypropylene and polyethylene are hydrophobic and provide a low fluorescence background. Amino groups may be introduced onto the polypropylene and polyethylene surface by using a plasma discharge in an ammonia or organic-amine-containing gas, as described above.

The assay article of the present invention may be molded into a variety of shapes including, but not limited to, foams, filaments, threads, sheets, films, slides, gels, membranes, beads, plates, and like structures.

The biopolymer may be selected from the group consisting of nucleic acids, polypeptides, proteins, and analogues thereof. A probe biopolymer may be a polynucleotide, such as an amplified DNA, cDNA, RNA, or protein. A target biopolymer may be amplified DNA, cDNA, oligonucleotide, PNA, RNA or protein.

In a preferred embodiment, the substrate is made of an aminated polypropylene substrate in a form of a slide and the adsorbed biopolymer is a polynucleotide. Polynucleotides of various lengths may be directly adsorbed on the aminated polypropylene substrate. According to embodiments of the present invention, the length of the adsorbed polynucleotides may be from about 20 bp to about 10 kb. In order to achieve higher efficiency of adsorption, the length of the adsorbed polynucleotides is preferably between about 100 bp and about 10 kb.

Another aspect of the present invention provides a test kit for detecting a target biopolymer contained in a sample. The kit comprises an aminated polypropylene substrate and a probe biopolymer directly adsorbed on a surface of the substrate. When the probe polymer is contacted with the target biopolymer, they form a complex that can be detected by utilizing reporters and signal detection devices. The kit may also include a reporter for generating a signal, which indicates formation of the complex. Preferably, a plurality of the same or different biopolymers are attached to the substrate forming an array.

According to the present invention and as it is described above, the same or different biopolymers may be attached to the aminated polypropylene substrates to form an array.

The invention may be better understood with reference to the accompanying example that is intended for purposes of illustration only and should not be construed as, in any sense, limiting the scope of the present invention, as defined in the claims appended hereto. While the described procedures in the following example are typical of those that might be used, other procedures known to those skilled in the art may alternatively be utilized. Indeed, those of ordinary skill in the art can readily envision and produce further embodiments, based on the teachings herein, without undue experimentation.

EXAMPLE 1

Preparation of cDNA Arrays

Polypropylene slides were surface aminated by a radio-frequency discharge into ammonia gas, as described in Coassin et al. (U.S. Pat. No. 5,554,501, assigned to the assignee of the present invention). Unmodified cDNA of actin, β-microglobulin, G3PDH, p53, and TNF-a genes were prepared each at a final concentration of InM in 50 mnM sodium bicarbonate buffer, pH 9. A Biomek 2000™ robotic system (Beckman Coulter, Inc., CA) equipped with a 384-pin HDRT system (Beckman Coulter, Inc., CA) was used to apply 10 nl aliquots of cDNA solutions onto the aminated polypropylene slides. A set of 5-(Biotinamido)pentylamine (BAPA) markers, (Pierce Chemical, IL), were also printed at both ends of each slide, thereby flanking the cDNAs. BAPA, which binds streptavidin-enzyme conjugate independently of hybridization, serves as an internal control for assay robustness. Following the application of the cDNA and BAPA markers, the slides were dried at 35° C. for 15 minutes. Then the slides were either soaked in ethanol for one hour or in ammonium hydroxide for 15 minutes to remove loosely bound nucleic acid. Then, the slides were briefly rinsed with water and air-dried. In one case, an ethanol-quenched slide was further rinsed in 1M NaOH for 15 minutes. The slides were stored at −20° C. overnight.

Hybridization

For hybridization, each slide was brought to a room temperature and denatured for 15 minutes in 0.15M NaCl and 0.5M NaOH solution. A mixture of biotin-labeled cDNA targets of actin, β-microglobulin, G3PDH, and p53 were applied at a final concentration of 0.5 nM, following denaturation and the addition of hybridization buffer (2.4×SSC, 0.016% SDS, 0.28M TRIS, 0.028 NaCl, pH 7.5). The TNF-α target was not added so that non-specific hybridization could be measured to the TNF-α probe. Hybridization was allowed to proceed for 1 hour at 60° C., followed by a stringency rinse in 2×SSC, 0.01% SDS at the same temperature. The slides were incubated with streptavidin-alkaline phosphatase, and ELF reagent (fluorescent substrate for alkaline phosphatase) for 30 min. Following the incubation, the fluorescent signal image was recorded using a CCD camera.

Results

An array of cDNA and BAPA markers were successfully adsorbed on the aminated polypropylene slides, as determined by hybridization of a mixture of the corresponding cDNAs (FIG. 1). FIG. 1 shows Biomek HDRT printing of cDNA and BAPA markers onto aminated polypropylene slides. The TNF-α signal was absent (negative control), while the remaining cDNA hybridization signals remained approximately at the same intensity as the signals from the BAPA markers (positive control). The signal from the ammonium-hydroxide-quenched slide was significantly reduced in the intensity over that of the ethanol-quenched slides. There was no significant difference between ethanol- vs. ethanol-NaOH-pretreated slides. This example illustrates that plasma aminated polypropylene slides are capable of direct and stable adsorption of cDNA without chemical crosslinking.

Thus, the aminated polypropylene slides with directly adsorbed biopolymers of the present invention and the method of their use in detection of target biopolymers are well adapted to attain all of the ends and objects set forth above, together with other advantages, which are inherent to the system. The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes which come within the meaning and range of the equivalence of the claims are to be embraced within their scope.

EXAMPLE 2

Preparation of Protein Array

Human IgG attachment: Polypropylene film was surface aminated by a radio-frequency discharge as described in Example 1. Diluted Human IgG (Pierce Chemicals, cat. # 31877, 28 mg/mL) stock to 1 mg/mL in sodium bicarbonate (50 mM, pH 9) and 4% sodium sulfate. Twenty-one 0.5 μL spots were pipetted onto an amino polypropylene strip 2 cm wide and 8 cm long. Attachment reaction was allowed to proceed for 60 min. at 25° C. The film was rinsed with Casein solution (1 mg/mL in 50 mM sodium carbonate, 0.15M NaCl pH 9) for 60 min. at 25° C., and then rinsed twice in deionized water and by 1×TBS, 0.02% Tween-20, pH 7.4 briefly. The strip was then used for binding assay.

Conjugation with goat anti-human IgG alkaline phosphatase: The 200 μL of diluted goat anti-human IgG alkaline phosphatase (Pierce Chemicals. cat. # 31310) solution 1:1000 in blocking buffer (1×TBS, 1 mg/mL Casein, 0.02% Tween-20 pH 7.4) was pipetted to a petri dish and the above-spotted polypropylene strip was placed on it. Spotted side of the polypropylene strip down, on top of the solution and was incubated for 60 min. at 25° C. The polypropylene strip was then rinsed 4 times in 20 mL of 1×TBS, 0.02% Tween-20, pH 7.4.

ELF detection: To detect the fluorescence signal, the enzyme substrate, ELF, was prepared by mixing components A and B (1:25) (Molecular Probes, Eugene, Oreg.) and 200 μL solution for each strip was used as described above. After 30 min. incubation at 22° C., the strip was dipped once in deionized water. The signals were detected using 365 nm UV light and a CCD camera, having 520 nm filter as shown in FIG. 2.

Results

Figure 2:
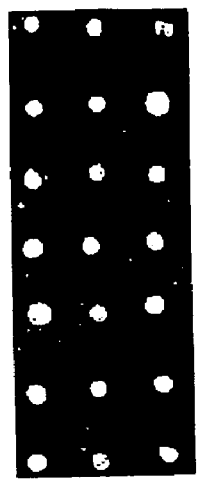
FIG. 2 shows attachment of human IgG to aminated polypropylene support.

An array of IgG was successfully adsorbed on the aminated polypropylene film as shown in FIG. 2.

Thus, the aminated polypropylene slides with directly adsorbed biopolymers of the present invention and the method of their use in detection of target biopolymers are well adapted to attain all of the ends and objects set forth above, together with other advantages, which are inherent to the system. The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes which come within the meaning and range of the equivalence of the claims are to be embraced within their scope.

What is claimed is:

1. A method of detecting a target biopolymer contained in a sample, comprising the steps of:
   (a) providing a substrate with a surface;
   (b) modifying the surface of the substrate by introducing a functionality selected from a group consisting of amino group, carboxyl group, and thiol group on the surface to obtain a modified surface;
   (c) providing a probe biopolymer that can form a complex with the target biopolymer;
   (d) contacting either the probe or target biopolymer with the modified surface of the substrate and drying the substrate whereby either the probe or target biopolymer directly adsorbs and immobilizes on the modified surface without additional fixing steps and without chemical crosslinking to form a probe assay article or a target assay article, respectively;
   (e) contacting the probe assay article with the target biopolymer, or contacting the target assay article with the probe biopolymer under a condition that allows the formation of a complex comprising the probe and the target biopolymers; and
   (f) detecting and determining the presence of the complex as a measurement for the presence or the amount of the target biopolymer contained in the sample.

2. The method of claim 1, wherein the modified surface is an amino-modified surface.

3. The method of claim 2, wherein the substrate with amino-modified surface is amino polypropylene.

4. The method of claim 1, wherein each of the target and the probe biopolymers are selected from a group consisting of nucleic acids, polypeptides, proteins, and analogues thereof.

5. The method of claim 1, wherein the target biopolymer is a target polynucleotide, and the probe biopolymer is a polynucleotide that is complementary to the target polynucleotide.

6. The method of claim 5, wherein the complex further comprises a reporter selected from the group consisting of dyes, chemiluminescent compounds, enzymes, fluorescent compounds, metal complexes, magnetic particles, biotin, haptens, radio frequency transmitters, and radioluminescent compounds.

7. The method of claim 6, wherein the biopolymer is a polynucleotide, the reporter is biotin, and the method of claim 6 further comprises a step of incubating the complex adsorbed on the modified surface of the substrate with streptavidin-alkaline phosphatase and an ELF reagent for developing a fluorescent signal prior to the detecting step.

8. The method of claim 7, wherein the modified surface is an amino-modified surface.

9. The method of claim 8, wherein the substrate with the amino-modified surface is amino polypropylene.

10. The method of claim 1, wherein the same or different probe or target biopolymers are adsorbed on discrete, isolated areas on the modified surface to form an array.

11. The method of claim 10, wherein the detecting step comprises recording the signal with a confocal array reader.

12. The method of claim 11, wherein the signal is a fluorescence and the confocal array reader is a CCD camera.

13. The method of claim 1, wherein the substrate is made of polypropylene or polyethylene.

14. The method of claim 13, wherein the modifying step comprises animating the surface of the substrate.

15. The method of claim 1, wherein the probe biopolymer or the target biopolymer of step (c) is unmodified.

16. The method of claim 1, wherein the probe biopolymer or the target biopolymer of step (c) is modified.

17. The method of claim 1, wherein the amount of the probe biopolymer or the target biopolymer contacted with the modified surface in step (c) ranges from about 10–20 to about 10–14 moles.

18. The method of claim 17, wherein the probe biopolymer or the target biopolymer is a polynucleotide, and the amount of the polynucleotide is about 10–18 moles.

19. The method of claim 17, wherein the contacting step (c) comprises placing an aliquot of the probe biopolymer or the target biopolymer solution on the modified surface, wherein the aliquot is from about 0.1 nL to about 500 nL.

20. The method of claim 19, wherein the probe biopolymer or the target biopolymer is a polynucleotide, and the aliquot is about 10 nl.

21. The method of claim 1, wherein the drying is air-drying conducted for a period ranging from about 5 minutes to about 60 minutes.

22. The method of claim 21, wherein the air-drying is conducted for a period of about 15 min.

23. A method of detecting a polypeptide contained in a sample, comprising the steps of:
   (a) providing a substrate with a surface;
   (b) modifying the surface of the substrate by introducing a functionality selected from a group consisting of amino group, carboxyl group, and thiol group on the surface to obtain a modified surface;
   (c) providing a probe polypeptide that can form a complex with the target polypeptide;
   (d) contacting either the probe or target polypeptide with the modified surface of the substrate and drying the substrate whereby either the probe or target polypeptide directly adsorbs and immobilizes on the modified surface without additional fixing steps and without chemical crosslinking to form a probe assay article or a target assay article, respectively;
   (e) contacting the probe assay article with the target polypeptide, or contacting the target assay article with the probe polypeptide under a condition that allows the formation of a complex comprising the probe and the target polypeptides; and
   (f) detecting and determining the presence of the complex as a measurement for the presence or the amount of the target polypeptide contained in the sample.

24. The method of claim 23, wherein the probe polypeptide is a protein.

25. The method of claim 23, wherein the target polypeptide is a protein.

26. The method of claim 23, wherein the amount of the probe polypeptide or the target polypeptide contacted with the modified surface in step (c) ranges from about 10–20 to about 10–14 moles.

27. The method of claim 23, wherein the aliquot is from about 0.1 nL to about 500 nL.

28. The method of claim 23, wherein the drying is air-drying conducted for a period ranging from about 5 minutes to about 60 minutes.

29. The method of claim 23 further comprising washing the probe assay article or the target assay article to remove loosely bound probe or target polypeptides, respectively, wherein the washing is conducted immediately after the drying step is completed.

* * * * *